(12) United States Patent
Dubois et al.

(10) Patent No.: US 7,791,739 B2
(45) Date of Patent: Sep. 7, 2010

(54) SYSTEM AND METHOD TO ENABLE EYE-SAFE LASER ULTRASOUND DETECTION

(75) Inventors: Marc Dubois, Clifton Park, NY (US); John B. Deaton, Jr., Niskayuna, NY (US); Thomas E. Drake, Jr., Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 341 days.

(21) Appl. No.: 10/828,068

(22) Filed: Apr. 20, 2004

(65) Prior Publication Data

US 2005/0231735 A1   Oct. 20, 2005

(51) Int. Cl.
*G01B 11/14* (2006.01)
(52) U.S. Cl. .................. 356/614; 356/237; 356/4.01
(58) Field of Classification Search ............. 356/614, 356/237, 502, 237.1–237.5, 4.01
See application file for complete search history.

(56) References Cited

U.S. PATENT DOCUMENTS

| | | | | |
|---|---|---|---|---|
| 4,890,925 A * | 1/1990 | Kitamori et al. | ............. | 356/432 |
| 5,153,667 A * | 10/1992 | Aoshima et al. | ............. | 356/218 |
| 5,181,211 A * | 1/1993 | Burnham et al. | ............. | 372/21 |
| 5,381,430 A * | 1/1995 | Nozaki et al. | ............. | 372/21 |
| 5,402,434 A * | 3/1995 | Manako et al. | ............. | 372/41 |
| 5,831,718 A | 11/1998 | Desai et al. | ............. | 356/5.01 |
| 5,926,273 A * | 7/1999 | Kimura et al. | ............. | 356/502 |
| 6,031,853 A * | 2/2000 | Greene et al. | ............. | 372/22 |
| 6,122,060 A * | 9/2000 | Drake, Jr. | ............. | 356/502 |
| 6,141,650 A * | 10/2000 | Iwasa et al. | ............. | 705/19 |
| 6,142,650 A | 11/2000 | Brown et al. | ............. | 362/259 |
| 6,335,943 B1 * | 1/2002 | Lorraine et al. | ............. | 372/28 |
| 6,431,731 B1 * | 8/2002 | Krietzman | ............. | 362/259 |
| 6,486,962 B1 * | 11/2002 | Telschow et al. | ............. | 356/503 |
| 6,580,732 B1 * | 6/2003 | Guch et al. | ............. | 372/18 |
| 6,813,951 B2 * | 11/2004 | Blouin et al. | ............. | 73/643 |
| 2002/0140215 A1 * | 10/2002 | Breed et al. | ............. | 280/735 |
| 2004/0021930 A1 * | 2/2004 | Pfeiffer et al. | ............. | 359/330 |
| 2004/0036975 A1 | 2/2004 | Slatkine | ............. | 359/584 |
| 2004/0057056 A1 * | 3/2004 | Drake, Jr. | ............. | 356/511 |
| 2004/0218652 A1 * | 11/2004 | Spariosu et al. | ............. | 372/70 |
| 2005/0099634 A1 * | 5/2005 | Dubois et al. | ............. | 356/502 |
| 2005/0234527 A1 * | 10/2005 | Slatkine | ............. | 607/89 |

FOREIGN PATENT DOCUMENTS

EP   0 806 822 A1   11/1997

\* cited by examiner

*Primary Examiner*—Tarifur R. Chowdhury
*Assistant Examiner*—Isiaka O Akanbi
(74) *Attorney, Agent, or Firm*—Bracewell & Giuliani LLP

(57) ABSTRACT

A system and method that replaces safety requirements of a laser detection system by shifting the wavelength of a detection laser. An optical wavelength converter that shifts the optical wavelength of a detection laser from a first wavelength within the Infrared "A" portion of the spectrum to a more eye-safe wavelength. The detection laser is directed to the surface of a remote target. Ultrasonic displacements at the surface scatter the filtered detection laser. Collection optics then gather phase modulated light scattered by the surface and direct the phase modulated light to an optical processor that produces a signal representative of the ultrasonic displacements. Signal processors then determine the internal structure of the remote target based on the signal.

17 Claims, 4 Drawing Sheets

US 7,791,739 B2

SYSTEM AND METHOD TO ENABLE EYE-SAFE LASER ULTRASOUND DETECTION

TECHNICAL FIELD OF THE INVENTION

The present invention relates generally to the generation and detection of ultrasound in materials using lasers, and more particularly, to a system and method for changing the optical wavelength of the detection laser to a more eye-safe wavelength.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in both the manufacturing processes and after the materials are in service in finished products. Specifically, non-destructive evaluation (NDE) methods must assess the structural integrity of composite materials. This assessment detects inclusions, delaminations and porosities. Conventional NDE methods are slow, labor-intensive, and costly. As a result, testing procedures adversely increase the manufacturing costs associated with composite structures.

Various methods and apparatuses have been proposed to assess the structural integrity of composite structures. One test method uses ultrasound and lasers. An external ultrasound source generates ultrasonic surface displacements in a work piece, and laser light from a detection laser is directed at the work piece. Ultrasonic surface displacements scatter the detection laser beam, and collection optics collect the scattered laser energy. The collection optics are coupled to an interferometer or other device, and data about the structural integrity of the composite structure can be obtained.

Laser ultrasound has been shown to be very effective for the inspection of parts during the manufacturing process. However, the wavelength of the detection laser used for detection of ultrasonic displacements is very often around 1 μm (1.064 μm for Nd:YAG lasers). This wavelength is very harmful to the human eye and exposure causes severe retinal damage. Because of this, strict laser safety precautions must be observed when using these laser detection systems. These precautions include engineering controls (physical barriers, interlocks, sensors) administrative controls (warning signs, policies, procedures), and personal protective equipment (PPE)(goggles, helmets, clothing). Engineering controls are often employed within industrial environments. Generally these controls involve placing the inspection facility in a closed room within a plant. This solution confines laser ultrasound inspection to a few locations in a plant for manufacturing. For other applications, like in-service inspection, a closed-room solution might not be practical or possible.

Different wavelengths of light have different physiological effects and require different safety precautions. Replacing the existing detection laser source with a more eye-safe laser source may not be practical or cost-effective.

Therefore a need exists for an effective and economical means in which more relaxed laser safety constraints may be employed with these detection lasers.

SUMMARY OF THE INVENTION

The present invention provides a laser ultrasound system that substantially eliminates or reduces disadvantages and problems associated with previously developed detection lasers for ultrasound systems. More specifically, the present invention shifts the detection laser's wavelength within a laser ultrasound detection to substantially address these needs and others. The system includes an external ultrasound source that produces ultrasonic displacements at the surface of a remote target, such as a composite material under test. This external ultrasound source may be a pulsed laser beam or other like means to generate ultrasonic displacements as known to those skilled in the art. A detection laser generates a detection laser beam to detect ultrasonic displacements at the surface. Then, an optical wavelength or frequency converter shifts the wavelength of the detection laser beam to a more eye-safe wavelength.

In one embodiment, the optical wavelength converter may be a non-linear optical wavelength converter. Such non-linear optical wavelength converters include an optical parametric oscillator, an optical parametric amplifier, a difference frequency generator, a sum frequency generator, or other non-linear optical filters known by those skilled in the art. The non-linear optical filter may be employed in a phase-matched configuration or a non-phase-matched configuration. Furthermore, the non-linear optical filter may employ an input-seeding beam.

By converting the optical wavelength of the detection laser beam to a more eye-safe wavelength, such as 1.55 μm, the need for stringent laser safety requirements can be reduced or eliminated. This allows laser ultrasound inspections to be performed in far more locations with relaxed laser safety requirements. This enables the use of laser ultrasound inspection systems at virtually any location within the manufacturing environment. Furthermore, relaxed laser safety requirements enable the use of laser ultrasound inspection equipment for in-service inspection of materials in field environments not designed for laser safety, such as aircraft hangers or outdoors. Thus, the present invention may allow greater use of laser ultrasound to inspect materials without risking worker eye safety.

After conversion to an eye-safe wavelength, the detection laser beam is directed to the surface of a remote target, where the laser beam interacts with the ultrasonic displacements to produce phase modulated light. This phase modulated light, scattered or reflected at the surface of the target, is collected for optical processing. An interferometer or other optical processing device then processes the collected phase modulated light to generate an output signal containing data representative of the ultrasonic surface displacements on the surface of the remote target. This signal may be further processed to reveal the internal structure of the remote target.

The present invention provides an important technical advantage by reducing or eliminating the need for laser safety measures such as engineering controls, administrative controls and personal protective equipment. This provides greater worker safety and enables the use of laser ultrasound equipment in more environments. Additionally, existing laser ultrasound equipment may be easily modified to operate with reduced laser safety measures without replacing the equipment's existing detection laser. Rather, only the optical wavelength or frequency converter need be placed in the path of the detection laser beam of existing laser detection systems.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGUREs, like numerals being used to refer to like and corresponding parts of the various drawings.

Figure 1:
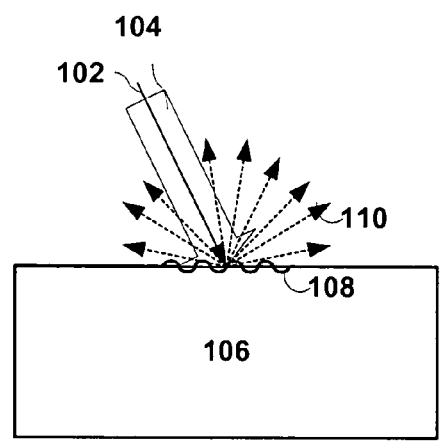
FIG. 1 illustrates the generation and detection of ultrasound with a laser beam.

FIG. 1 illustrates two incoming laser beams that strike a material under test. Laser beam 102 generates ultrasound. The ultrasonic displacements are illuminated by laser beam 104. The illumination laser allows ultrasound at remote target 106 to be detected. The remote target may be a composite material. These lasers may be coaxially applied to remote target 106. Generation laser beam 102 causes thermoelastic expansion in target 106 in the form of ultrasonic deformations 108. Deformations 108 modulate, scatter and reflect illumination laser beam 104 to produce phase-modulated light 110 directed away from target 106.

Figure 2:
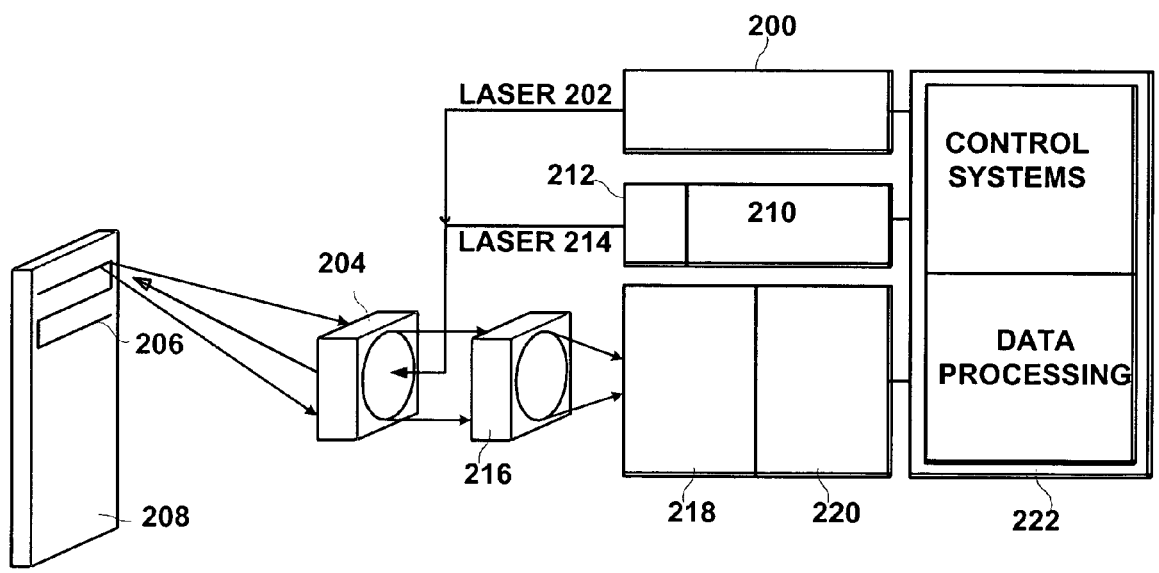
FIG. 2 is a block diagram showing the basic components of an eye-safe laser ultrasound system in accordance with one embodiment of the present invention.

FIG. 2 is a block diagram that shows the basic components for performing eye-safe ultrasonic laser testing. An external ultrasound source generates ultrasonic displacements in a remote target. In this example, laser energy generates ultrasonic displacements. Generation laser 200 produces a laser beam 202 which optical assembly 204 then directs to composite material 208. As shown, optical assembly 204 includes a scanner or other like mechanism that moves laser beam 202 along a scan or test plan 206. Generation laser beam 202 produces a compressional ultrasonic wave in target 208.

The compressional ultrasonic wave is the result of thermoelastic expansion of the composite material as the material absorbs the generation laser beam. Composite material 208 readily absorbs generation laser beam 202 without ablating or breaking down. Generation laser beam 202 has an appropriate pulse duration to induce ultrasonic surface deformations. Generation laser beam 202 is absorbed as heat into the target surface thereby causing thermoelastic expansion without ablation.

Figure 3:
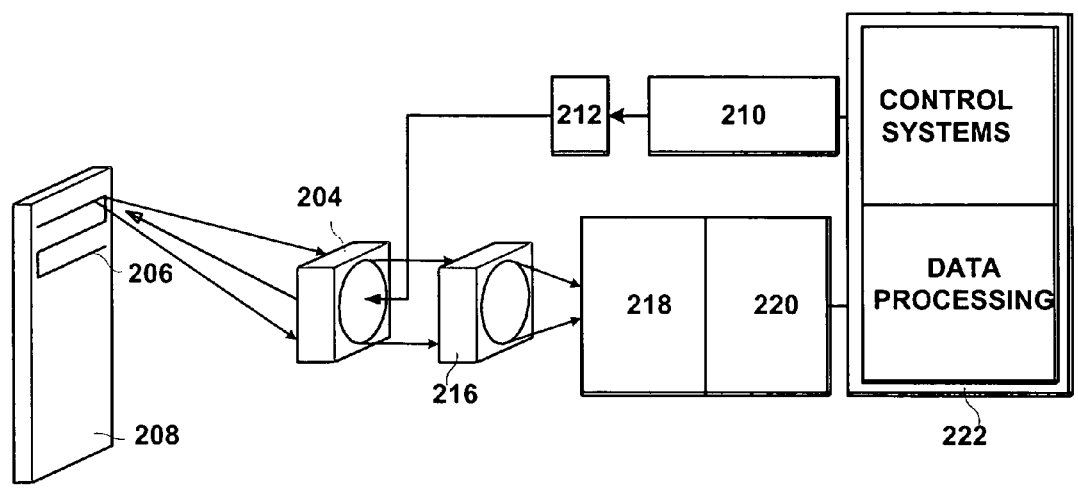
FIG. 3 is a block diagram depicting a detection laser beam used to detect ultrasonic displacements within an eye-safe laser ultrasound system in accordance with one embodiment of the present invention.

FIG. 3 provides a block diagram of another embodiment of an eye-safe laser ultrasound detection system. This system is similar to the one discussed in reference to FIG. 2 with the exception that a laser is not used to generate the ultrasound of FIG. 3. Here ultrasonic displacements may be generated within material 208 by other known means. These means include, but are not limited to, mechanically coupling a transducer to material 208. Other means known to those skilled in the art may be employed.

In both FIGS. 2 and 3, detection laser 210 generates a detection laser beam to detect ultrasonic surface displacements. Detection laser 210 has an appropriate power and pulse duration to not induce ultrasonic displacements. In one embodiment, an Nd:YAG laser can be used. An Nd:YAG laser produces laser light with a wavelength of 1.064 μm, which is harmful to the human eye. Generally, the detection laser is more harmful than the generation laser. This is due to the fact that the detection laser beam's wavelength is in the near infrared.

Optical wavelength converter 212 converts detection laser beam 214 to a more eye-safe wavelength, such as 1.55 μm. By converting the optical wavelength of the detection laser beam to a more eye-safe wavelength, such as 1.55 μm, the need for stringent laser safety requirements can be reduced or eliminated. This allows laser ultrasound inspections, or other applications that employ a detection laser within the infrared "A" portion of the spectrum, be performed in far more locations. Relaxed laser safety requirements in manufacturing environments enable the use of laser ultrasound inspection systems at virtually any location in the manufacturing plant. Relaxed laser safety requirements enable the use of laser ultrasound inspection equipment for in-service inspection of materials in field environments not designed for laser safety, such as aircraft hangers or outdoors. This allows greater use of laser ultrasound to inspect materials without risking worker eye safety.

Once the wavelength of detection laser beam 214 has been shifted, laser beam 214 exits optical wavelength converter 212 and enters optical assembly 204. Optical assembly 204 directs converted detection laser beam 214 to the surface of composite material 208, which scatters and/or reflects converted detection laser beam 214. Resultant phase modulated light is collected by collection optics 216. Optical processors 218, such as interferometer 220, process the phase modulated light to produce a signal containing information representative of the ultrasonic displacements at the surface of composite material 208. Data processing and control system 222 coordinate operation of the laser ultrasound system components.

Data processing and control system 222 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. The memory stores, and data processing and control system 222 executes, operational instructions corresponding to at least some of the steps and/or functions as will be illustrated in FIG. 7.

Figure 4:
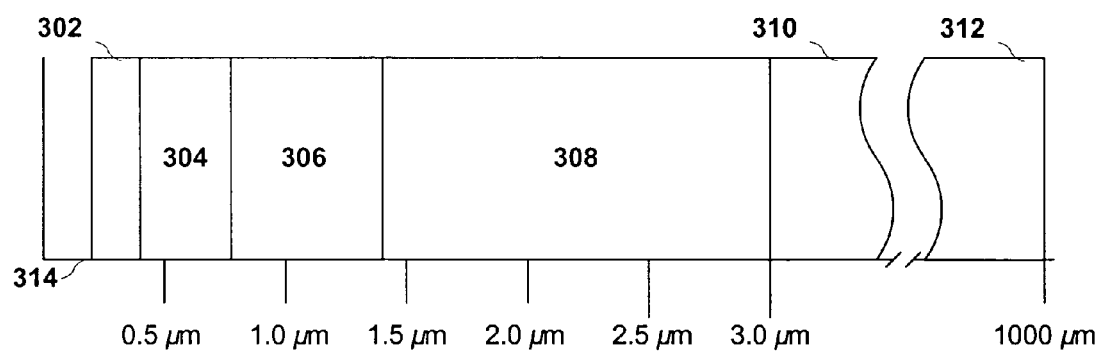
FIG. 4 is a graphic depiction of the electromagnetic spectrum from 0 to 1000 μm.

FIG. 4 depicts a portion of the electromagnetic spectrum with wavelength between 0 μm to 1000 μm. Section 302 depicts the ultraviolet light spectrum, ranging from 0.2 μm to 0.4 μm. Section 304 depicts the visible light spectrum, ranging from 0.400 μm to 0.780 μm. Section 306 depicts the Infrared "A" spectrum, ranging from 0.780 μm to 1.400 μm. Section 308 depicts the Infrared "B" spectrum, ranging from 1.400 μm to 3.000 μm. Sections 310 and 312 depict the beginning and ending of the Infrared "C" portion of the spectrum that starts at 3.000 μm and ends at 1000.000 μm. Horizontal axis 314 indicates the wavelength from 0 μm to 1000 μm. The scale changes after 3 μm to allow greater detail to be viewed between 0 μm and 3 μm.

Figure 5:
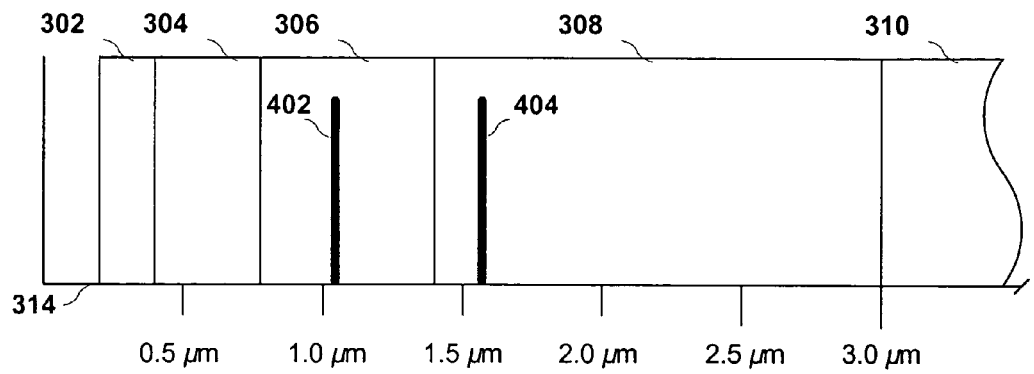
FIG. 5 is a graphic depiction of the wavelengths of detection laser light before and after the wavelength is shifted in accordance with one embodiment of the present invention.

FIG. 5 shows where the wavelengths of detection laser light are within the electromagnetic spectrum before and after wavelength is shifted. In this embodiment, detection laser beam 214 has a first wavelength of 1.064 μm, represented by line 402 and lies within the Infrared "A" portion of the spectrum. Line 404 represents a more eye-safe wavelength (1.550 μm) as the second wavelength of laser beam 214. This embodiment illustrates a shift specifically from 1.064 μm, within Infrared "A", to 1.550 μm, within Infrared "B" where retinal burns are less likely to occur. However, other shifts that result is reducing the potential for retinal burns or other like hazards are envisioned by the present invention.

Figure 6:
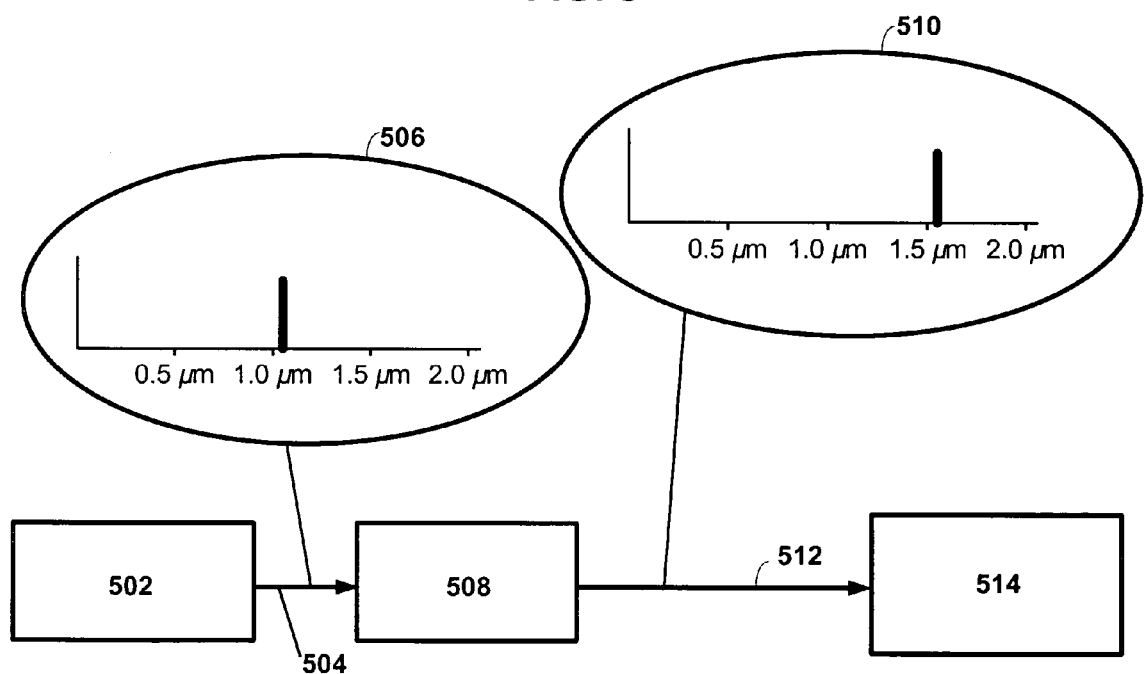
FIG. 6 shows a laser detection beam being converted from a harmful wavelength to a more eye-safe wavelength in accordance with one embodiment of the present invention.

FIG. 6 illustrates the process of converting a detection laser beam from a first wavelength to a second wavelength. In one instance this shift is from a hazardous wavelength in the near infrared to a more eye-safe wavelength. However, it should be noted that other reasons might exist to shift the wavelength of the detection laser. Depending on the reason for the shift, the second wavelength may be either longer or shorter than the first wavelength. As shown, the process of shifting the detection laser is depicted within a laser ultrasound system. Laser source 502 generates a detection laser beam 504. Callout 506 indicates the first wavelength of detection laser beam 504 as 1.064 μm. Optical wavelength converter 508 receives and processes detection laser beam 504 to produce detection laser beam 512. Converted detection laser beam 512 exits optical wavelength converter 508 with a wavelength of 1.550 μm as indicated by callout 510. Converted detection beam 512 enters optical assembly 512, which delivers laser beam 512 to the surface of a remote target for ultrasonic measurement.

Figure 7:
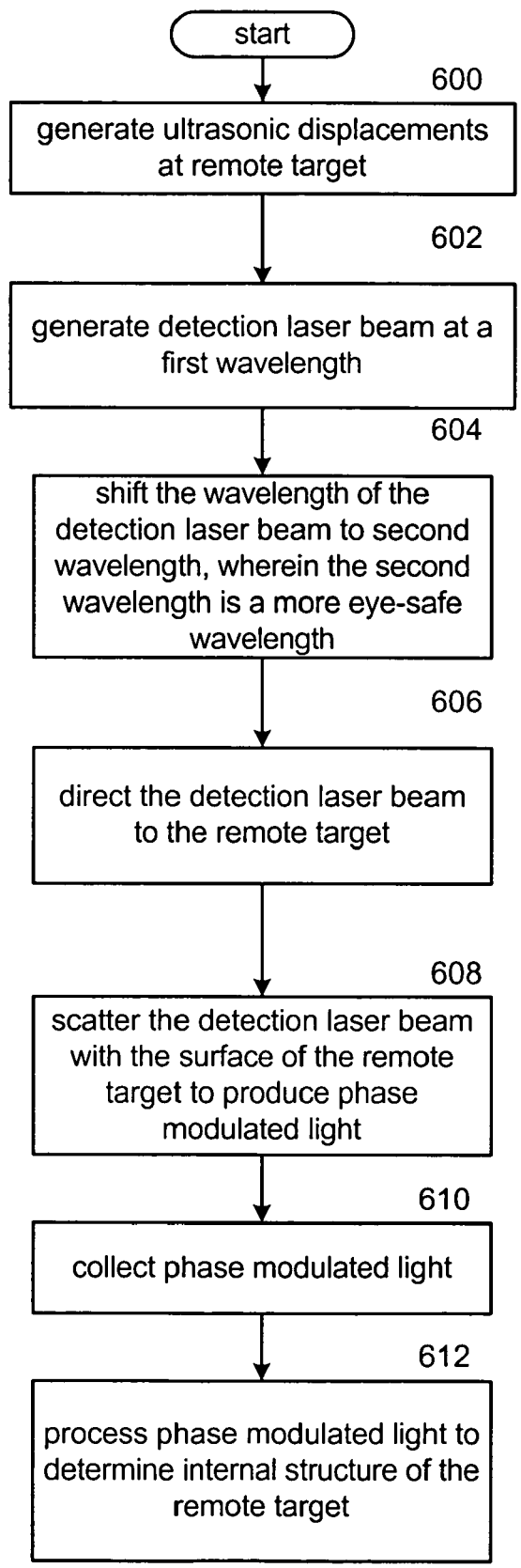
FIG. 7 is a logic flow diagram that depicts a method of detecting laser ultrasound with a detection laser shifted from a first wavelength to a second wavelength in accordance with one embodiment of the present invention.

FIG. 7 is a logic flow diagram that depicts a method of detecting laser ultrasound with a detection laser that is shifted from a first wavelength to a second wavelength in accordance with one embodiment of the present invention. Ultrasonic surface displacements are generated at a surface of the remote target in step 600. In step 602, a detection laser beam at a first wavelength is generated and then converted to a second wavelength in step 604, wherein the second wavelength is a more eye-safe wavelength. Step 604 may involve passing the detection laser beam through a non-linear optical wavelength converter. The non-linear optical wavelength converter may be selected from an optical parametric oscillator, an optical parametric amplifier, a difference frequency generator, a sum frequency generator or other like device known to those skilled in the art. In step 606, the detection laser beam is directed to the surface of the remote target. In step 608, the remote target then scatters the detection laser beam with ultrasonic surface displacements at its surface to produce phase-modulated light. The phase-modulated light is collected at step 610. Then the phase modulated light is processed in step 612 to obtain data representative of the ultrasonic surface displacements at the surface.

In operation the present invention allows laser ultrasonic test equipment to be used in a wider range of environments with relaxed laser safety requirements and greater eye safety for workers. The present invention also allows existing laser ultrasound equipment to be modified to operate with a safer laser wavelength without replacing the existing detection laser, an expensive component in the laser ultrasound system.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention is described in detail, it should be understood that various changes, substitutions and alterations can be made hereto without departing from the spirit and scope of the invention as described by the appended claims.

What is claimed is:

1. A method to inspect a composite material remote target comprising:

generating ultrasonic displacements in a surface of the remote target by directing a generation laser beam from a generation laser beam source to the remote target, the generation laser beam being at the same wavelength from the generation laser beam source to the remote target;

generating an infrared detection laser beam in a near infrared wavelength range between 0.780 to 1.400 microns;

converting the near infrared detection laser beam wavelength to an eye-safe infrared wavelength outside of the near infrared wavelength range;

directing the infrared eye-safe detection laser beam to the surface of the remote target;

scattering the infrared eye-safe detection laser beam with the ultrasonic surface displacements at the surface to produce phase modulated light;

collecting the phase modulated light; and processing the phase modulated light to obtain data representative of the ultrasonic surface displacements at the surface.

2. The method of claim 1, wherein converting the detection laser beam comprises passing the near infrared detection laser earn through a nonlinear optical wavelength converter selected from the group consisting of an optical parametric oscillator, an optical parametric amplifier, a difference frequency generator or a sum frequency generator so that the beam exiting the wavelength converter is an infrared eye-safe detection laser.

3. The method of claim 2, further comprising implementing the nonlinear optical wavelength converter to a configuration selected from the list consisting of a phase-matched configuration and a quasi-phase matched configuration.

4. The method of claim 2, further comprising configuring the nonlinear optical wavelength converter with an input-seeding beam.

5. The method of claim 1, wherein the near infrared detection laser beam is formed using an Nd:YAG laser and the eye-safe infrared detection laser beam wavelength is greater than 1.4 microns.

6. The method of claim 1, further comprising using a signal processor to determine the internal structure of the remote target based on the signal.

7. An apparatus for ultrasonically testing composite material of a target, the apparatus comprising:
- a generation laser source for generating a generating laser beam onto a surface of the target to create to create ultrasonic displacements in the surface of the target, the generation laser beam having a fixed wavelength from the generation laser source to the target;
- an infrared detection laser source that generates a detection laser beam having a wavelength in a near infrared range from 0.780 to 1.400 microns;
- an optical wavelength converter that receives the detection laser beam and converts the wavelength of the detection laser beam to a converted wavelength beam outside of the near infrared range, the converter being positioned to project the converted wavelength laser beam onto the ultrasonic displacements, the displacements forming phase modulated light reflecting from the surface of the target;
- collection optics that receives the phase modulated light, the collection optics having an interferometer;
- an output signal exiting an output of the interferometer; and
- a processor in signal communication with the output of the interferometer, so that when the output signal exits the interferometer, the processor receives data representative of the ultrasonic surface displacements on the surface of the remote target.

8. The apparatus of claim 7, wherein the optical wavelength converter is a nonlinear optical wavelength converter selected from the group consisting of an optical parametric oscillator, an optical parametric amplifier, a difference frequency generator or a sum frequency generator.

9. The apparatus of claim 8, wherein the nonlinear optical wavelength converter is implemented in a configuration selected from the list consisting of a phase-matched configuration and a quasi-phase matched configuration.

10. The apparatus of claim 8, wherein the nonlinear optical wavelength converter is configured with an input seeding beam.

11. The apparatus of claim 7, wherein the detection laser source comprises an Nd:YAG laser.

12. The apparatus of claim 7, wherein the converted wavelength has a wavelength greater than 1.5 microns.

13. An eye-safe laser ultrasound detection system comprising:
- a generation laser beam source positioned to direct a generation laser beam against a surface of a composite remote target, the generation laser beam being the same wavelength from the generation laser beam source to the composite remote target to create ultrasonic displacements in the surface;
- a detection laser source to generate a near infrared detection laser beam with a wavelength in a near infrared range between 0.780 and 1.4 microns;
- An optical wavelength converter that receives the near infrared detection laser beam and converts the near infrared detection laser beam to an eye-safe infrared detection laser beam with wavelength range greater than 1.4 microns;
- an optical assembly disposed in the path of the eye-safe infrared detection laser beam for directing the eye-safe infrared detection laser beam to the ultrasonic displacements in the composite material remote target, so that phase modulated light is formed from the eye-safe infrared detection laser beam that reflects from the surface displacements;
- collection optics disposed in the phase modulated light path;
- an optical processor with an output signal comprising processed phase modulated light exiting the optical processor; and
- a signal processor adapted to receive the output signal, so that a signal can be created that is representative of the ultrasonic surface displacements on the surface of the remote target.

14. The eye-safe laser detection system of claim 13, wherein the optical wavelength converter is a nonlinear optical wavelength converter selected from the group consisting of an optical parametric oscillator, an optical parametric amplifier, a difference frequency generator or a sum frequency generator.

15. The eye-safe laser detection system of claim 14, wherein the nonlinear optical wavelength converter is implemented in a configuration selected from the list consisting of a phase-matched configuration and a quasi-phase matched configuration.

16. The eye-safe laser detection system of claim 14, wherein the nonlinear optical wavelength converter is configured with an input-seeding beam.

17. The eye-safe laser detection system of claim 13, wherein the near infrared detection laser beam is formed from an Nd:YAG laser.

* * * * *